United States Patent [19]
Mather et al.

[11] Patent Number: 5,118,194
[45] Date of Patent: Jun. 2, 1992

[54] OPTICAL INSPECTION OF LACQUER AND CARBON DEPOSITS

[75] Inventors: Bruce C. Mather; David S. McFalls, II; Douglas L. Michalsky, all of San Antonio, Tex.

[73] Assignee: Southwest Research Institute, San Antonio, Tex.

[21] Appl. No.: 700,346

[22] Filed: May 7, 1991

Related U.S. Application Data

[63] Continuation of Ser. No. 336,289, Apr. 11, 1989, abandoned.

[51] Int. Cl.⁵ .................. G01N 21/84; G01B 11/24
[52] U.S. Cl. .................... 356/426; 356/376; 356/446
[58] Field of Search ............. 356/73, 426, 445, 446, 356/376

[56] References Cited

U.S. PATENT DOCUMENTS

| | | | |
|---|---|---|---|
| 4,376,951 | 3/1983 | Miyazawa | 356/430 X |
| 4,555,635 | 11/1985 | Yoshida | 356/445 X |
| 4,559,684 | 12/1985 | Pryor | 356/376 X |

OTHER PUBLICATIONS

Luck et al., "New Methods for the Evaluation and Recording of Piston-Skirt Deposits," Society of Automotive Engineers Journal (Transactions) vol. 51 #Feb. 2 1943, pp. 38-44 & 63.

*Primary Examiner*—Vincent P. McGraw
*Attorney, Agent, or Firm*—Pravel, Gambrell, Hewitt, Kimball & Krieger

[57] ABSTRACT

An improved method and apparatus for classifying and quantifying lacquer and carbon deposits on internal combustion engine pistons. In the preferred embodiment of the invention, a piston is mounted on a rotating means and is rotated to expose the entire surface of the piston to a video imaging system. The piston is illuminated with indirect lighting in order to minimize reflections and to enhance the contrast of the video image. The video imaging system is comprised of a video camera which employs a charged coupled device (CCD) sensor and data storage for storing digital video produced by the camera. A microprocessor is operable to control operation of the camera and to process the stored data according to an algorithm to classify the video image into one of six categories.

3 Claims, 6 Drawing Sheets

OPTICAL INSPECTION OF LACQUER AND CARBON DEPOSITS

This is a continuation of co-pending application Ser. No. 07/336,289 filed on Apr. 11, 1989, now abandoned.

FIELD OF THE INVENTION

The present invention relates generally to the field of optical inspection systems and, more particularly, to a novel and improved technique for classifying and quantifying lacquer and carbon deposits on internal combustion engine pistons.

BACKGROUND

One of the problems encountered in systems employing hydrocarbon fuels is the build up over time of thermal oxide derived varnish-like lacquer deposits on the surfaces of combustion chambers and components of the fuel distribution network. One of the commonly used methods for rating an engine lubricant involves examination of a test piston which has been subjected to many hours of operation in a running engine. Lubricant efficacy can be measured, in part, by measuring the amount of lacquer and carbon which has been deposited on the piston surface (lands) and in the ring grooves. Currently, this evaluation procedure is done manually, using human judgement to classify the deposit color and coverage.

Currently lacquer deposits are categorized according to six classifications based on color: (1) clean (shiny aluminum, no deposits); (2) very light amber lacquer; (3) light amber lacquer; (4) amber lacquer; (5) dark brown lacquer; and (6) black lacquer. Each lacquer classification is slightly darker than the previous one, beginning with no lacquer deposit (clean) and ending with black (class 6 above). Under standards issued by the Coordinated Research Council (CRC) rating specification any lacquer deposit appearing to have a color value falling between two classes is given the higher class categorization. One of the difficulties with current inspection techniques is the use of subjective judgment on the part of the operator who classifies the lacquer deposit based on his individual perception of the "best match" to the color standard.

From the above discussion, it is clear that the prior art lacks an objective, precise and repeatable evaluation technique for evaluating lacquer and carbon deposits on surfaces of internal combustion engine. A method and apparatus of the present invention, discussed in more detail below, provides an efficient and effective inspection technique overcoming the difficulties of the prior art.

SUMMARY OF THE INVENTION

The present invention provides an improved method and apparatus for classifying and quantifying lacquer and carbon deposits on internal combustion engine pistons. In the preferred embodiment of the invention, a piston is mounted on a rotating means and is rotated to expose the entire surface of the piston to a video imaging system. The piston is illuminated with indirect lighting in order to minimize reflections and to enhance the contrast of the video image. The video imaging system is comprised of a video camera which employs a charged coupled device (CCD) sensor and data storage for storing digital video images produced by the camera. A microprocessor is operable to control operation of the camera and to process the stored data according to an algorithm to classify the video image into one of six categories.

DETAILED DESCRIPTION OF THE PREFERRED EMBODIMENT

Figure 1:
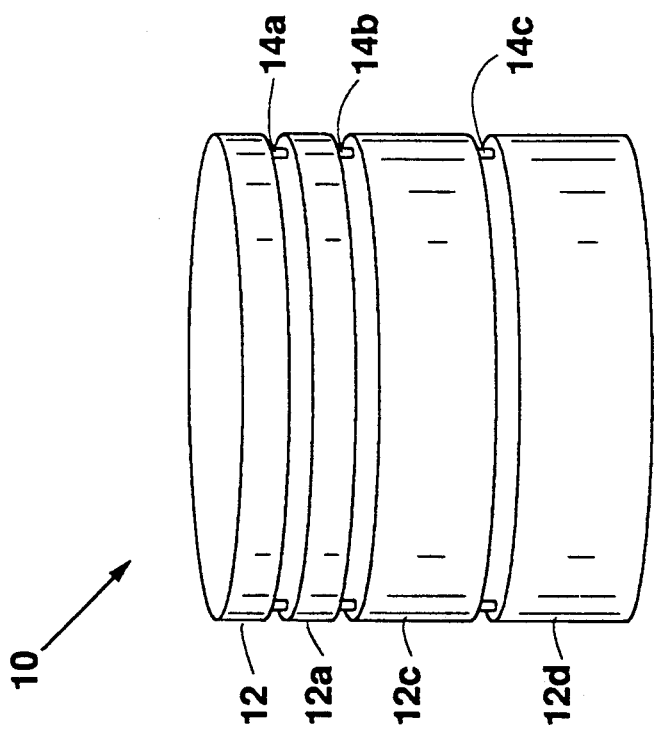
FIG. 1 is a perspective view of an internal combustion engine piston illustrating "land" and "groove" surfaces.

FIG. 1 is an illustration of an internal combustion engine piston of the type used to measure carbon and lacquer deposits in the inspection system of the present invention. The piston is comprised of a plurality of "lands" $12a$–$12d$ and a plurality of "grooves" $14a$–$14c$. The upper land area illustrated by reference numeral $12a$ is often referred to as the "crown" land of the piston.

Figure 2:
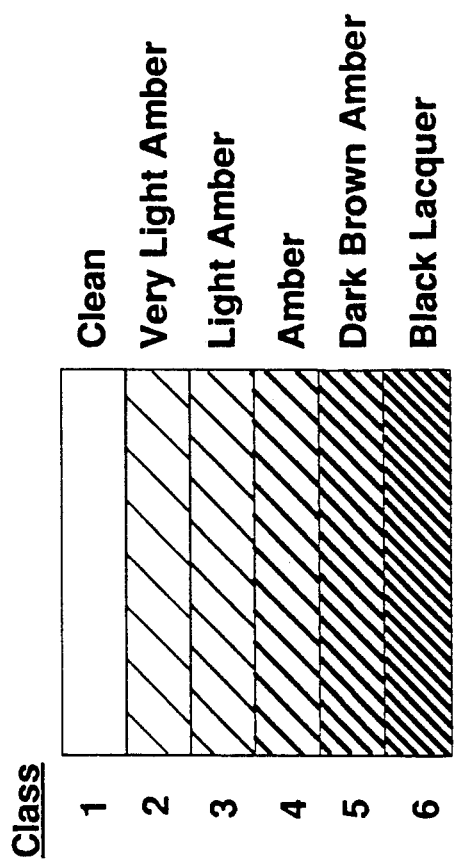
FIG. 2 is an illustration of a reference chip used to calibrate the inspection system of the present invention.

A rating reference chip 16, shown in FIG. 2, is used to calibrate the imaging system of the present invention, as will be discussed in greater detail below. This reference chip 16 is constructed from small strips of anodized aluminum, with each strip representing the equivalent lacquer color level corresponding to the CRC lacquer classification system. The reference chip 16 shown in FIG. 2 contains reference strips corresponding to each of the CRC rating categories: (1) clean (shiny aluminum, no deposits); (2) very light amber lacquer; (3) light amber lacquer; (4) amber lacquer; (5) dark brown lacquer; and (6) black lacquer. In the system, a video image of the reference chip is used to determine the reflectance intensity breakpoints to distinguish one lacquer class from another.

Figure 3:
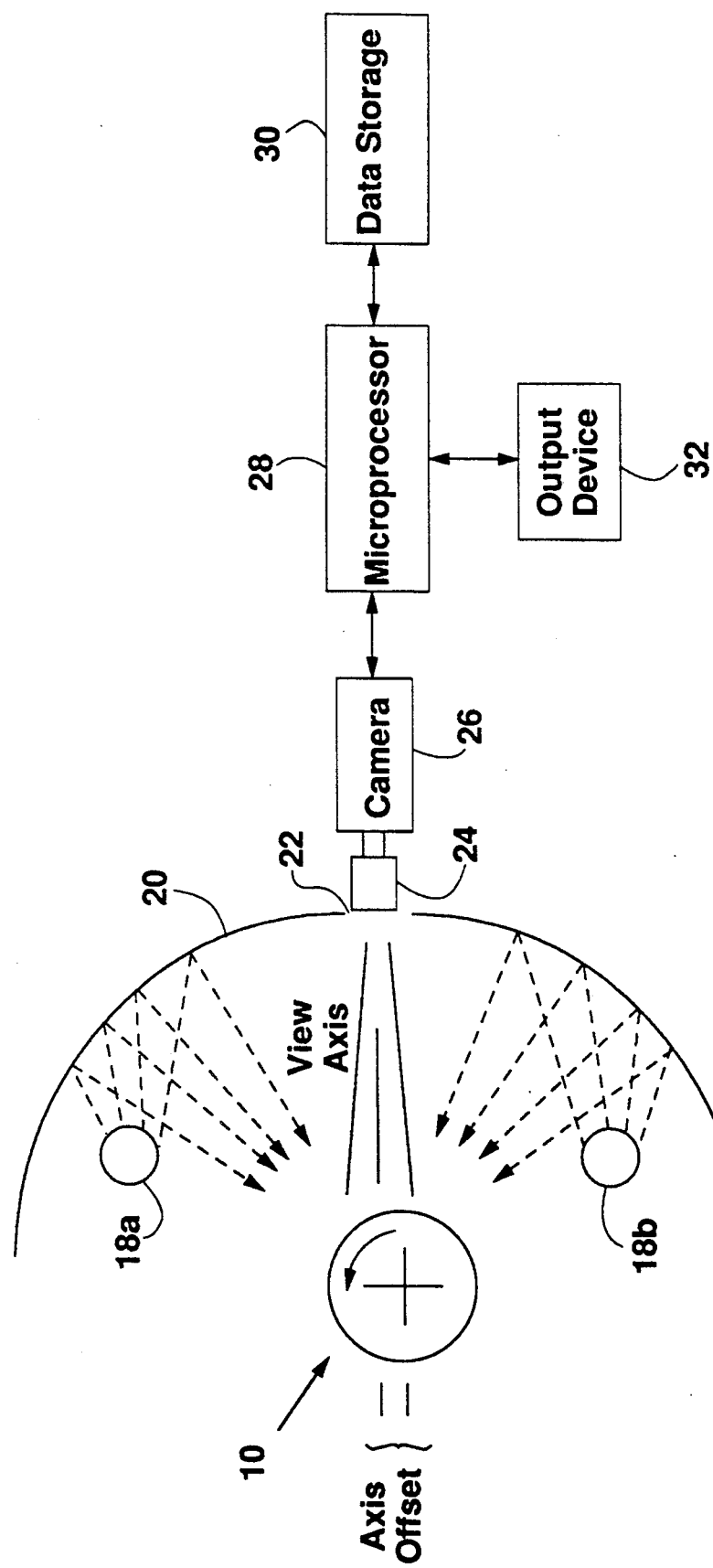
FIG. 3 is a plan view of an embodiment of the inspection system of the present invention utilizing a diffusing reflector.
Figure 4:
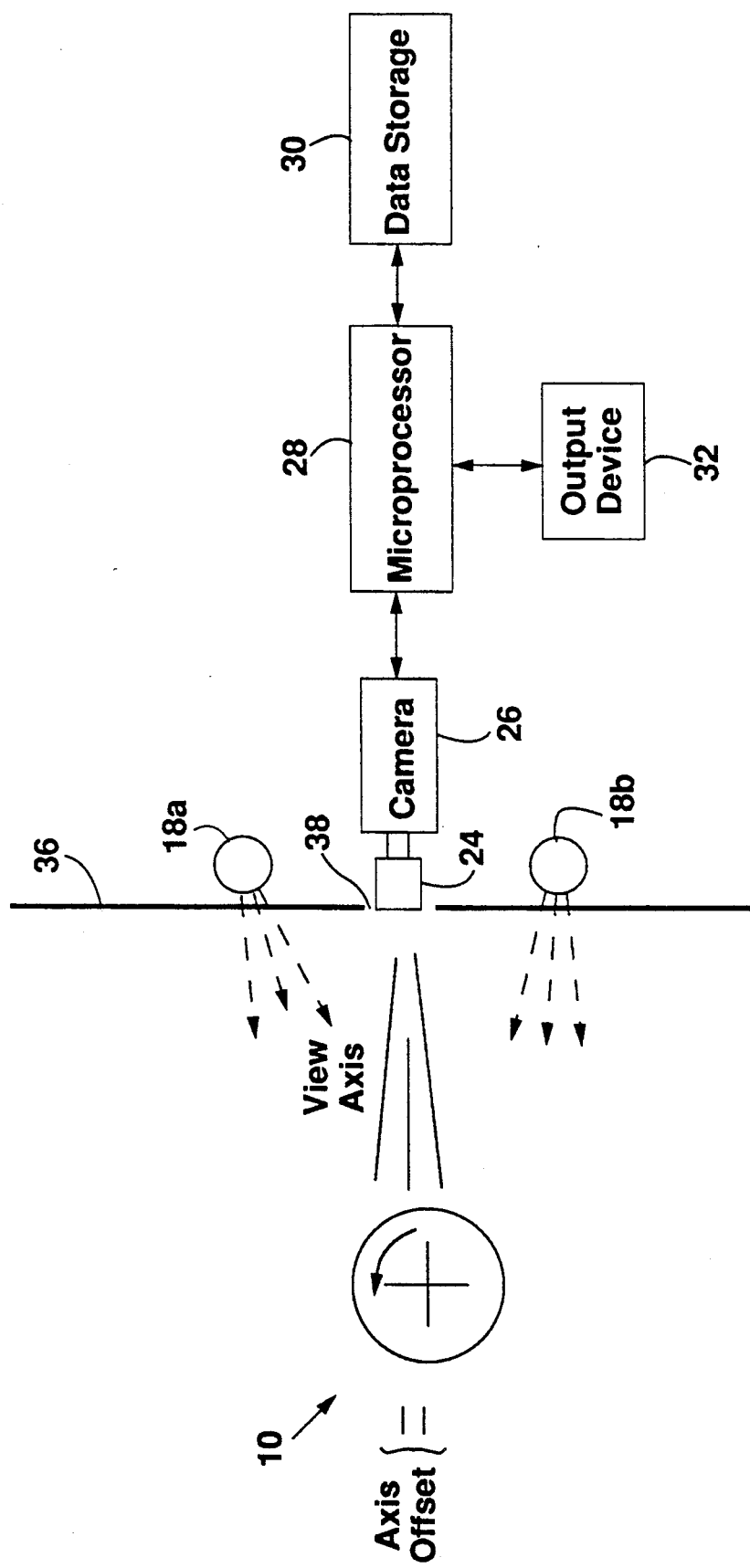
FIG. 4 is a plan view of an embodiment of the inspection system of the present invention utilizing a translucent panel.

The inspection system of the present invention is shown in FIGS. 3 and 4. The piston 10 is mounted on an appropriate means for rotating the piston to expose all of its surface area to the inspection system. The rotating means can be in the form of conventional electric motor, which rotates the piston at a constant velocity, or a "stepper" motor, which rotates the piston in discrete increments. The rotating means includes a platform which provides control of the piston (vertical) z-axis. The Z-axis control is used to position the piston inspection areas into the camera field-of-view. The field of view is either a land section or a groove. The rotational axis allows the piston surface to be "unwrapped" by successively acquiring images of the piston groove or land surface during rotation. The rotational speed of this axis is dependent on the required image capture and processing time. Typically the rotation speed will vary from ¼ rpm to 60 rpm.

The piston is illuminated by a plurality of lights, illustrated by light sources 18a and 18b. In the embodiment illustrated in FIG. 3, the light sources 18a and 18b are fluorescent lights. Optimum lighting is crucial in order to accurately separate the various lacquer color levels into distinct categories. It has been determined that an indirect diffuse lighting method produces the most uniform image with the greatest contrast. The geometry of the lighting used in the preferred embodiment is shown in FIG. 3. The light produced by the sources 18a and 18b is reflected by a cylindrical diffusing white reflector 20. This arrangement increases the uniformity of the lighting and minimizes shadows. The reflector 20 has an aperture 22 therein to receive the lens 24 of camera 26. Operation of the camera 26 is controlled by a microprocessor 28 which processes the video signal from the camera and stores the resulting data in data storage 30. Results of the data processing are displayed on a appropriate output device 32 which can be a conventional computer printer or a video display. The processing steps used to analyze the reference data and the video signal will be discussed in greater detail below.

An alternate embodiment of the lighting arrangement for the invention system is shown in FIG. 4. In this embodiment, a translucent panel 36 is placed between the light sources 18a and 18b and the piston 10. The translucent panel 36 is provided with an aperture 38 to receive the lens 24 of camera 26.

The camera 26 is a high resolution, black and white, camera employing a charge coupled device (CCD) sensor to obtain a digital representation of the piston reflectance. Each point on the piston surface under inspection is represented by an image picture element (pixel) with a value proportional to the reflected light intensity corresponding to that point. The pixels may take on integer values from 0 (black) to 255 (white). It is possible to use cameras having various spatial resolutions, for example, 256 by 240 or 512 by 480. In an alternate embodiment of the invention system, the CCD camera is replaced by a line scan camera which generates only a line of pixel data. In this embodiment, an image is created by passing the piston 10 past the camera at a controlled rate. The linescan camera is available at a variety of spatial resolutions. Excellent results were obtained in the invention system with a linecamera having a resolution of 512 pixels per line. Although the system can be operated with the camera axis centered on the piston axis, the camera 26 of the preferred embodiment is directed slightly off-center (approximately 1 centimeter) from the piston axis, as shown in FIGS. 3 and 4. This offset eliminates shadows caused by reflection of the camera lens on the shiny piston surface.

The reference chip 16, shown in FIG. 2, is imaged in order to calibrate the video system for lighting compensation and to create the table which maps image reflectance levels into lacquer classifications. One graylevel histogram is generated for each reference strip (six altogether) and a table created from this information is stored by microprocessor 28 in data storage 30. The microprocessor uses the processing steps discussed below to remap the pixel graylevels corresponding to the piston video signal into one of the six lacquer levels stored in memory.

There are several methods which are known in the art for generating the table breakpoints. For example, the successive graylevel breakpoints can be calculated as: 1) the histogram peak; 2) the midpoint between successive histogram peaks; 3) the midpoint between successive histogram means; 4) the overlap point between successive histogram tails; 5) linear combinations of the points listed above in methods (1)-(4). Once the upper and lower graylevel boundaries have been computed for each lacquer classification, the piston is imaged while rotating and each pixel (having an integer value ranging from zero to 255) is mapped into a lacquer category, i.e. a value from one to 6. The percentage coverage for each lacquer classification is then computed for each land and groove using standard percentage equations.

Figure 5:
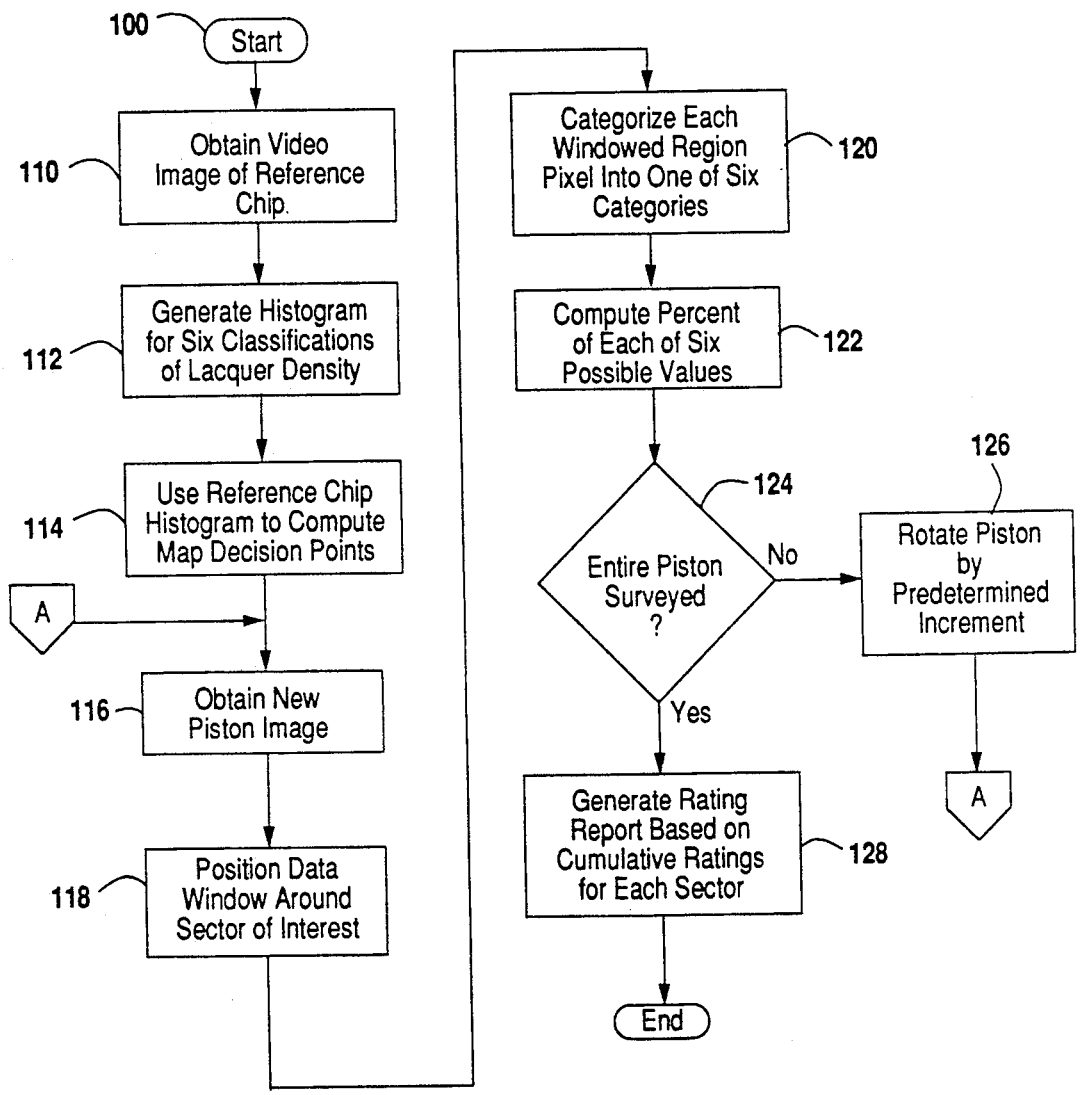
FIG. 5 is a flow chart of the data processing steps for rating a single land or groove implemented in the optical inspection system of the present invention.

The processing steps implemented by the microprocessor 28 can be understood be referring to the flowchart shown in FIG. 5. In step 100, the system is started. In step 110, a video image is obtained of the reference chip set. In step 114, the reference chip histogram is computed and the map decision breakpoints are determined according to one of the methods discussed hereinabove. These points delineate the chip graylevel boundaries. In step 116, an image is obtained of the piston land or groove to be rated. In the preferred embodiment of the invention, the piston circumference is divided into 18° sectors. In step 118, a data window is positioned around the land or groove sector of the image just obtained. In step 120, each of the pixels in the windowed region is sorted into one of six categories based on the decision point table determined in step 114. For purposes of this sorting procedure, an allowance for image saturation error is made. Saturated black is defined as a pixel value less than 5 and saturated white is defined as a pixel value greater than 250. In step 122, the system computes the percent of each of the six nonsaturated values found inside the rating widow. In step 124, a decision is made as to whether the entire piston has been surveyed. If the entire piston has not been surveyed, the piston is rotated by a predetermined increment in step 126 and steps 116 through 124 are repeated. If the determination of step 124 indicates that the entire piston has been surveyed, a report is generated based on the cumulative ratings for each sector in step 128.

Figure 6:
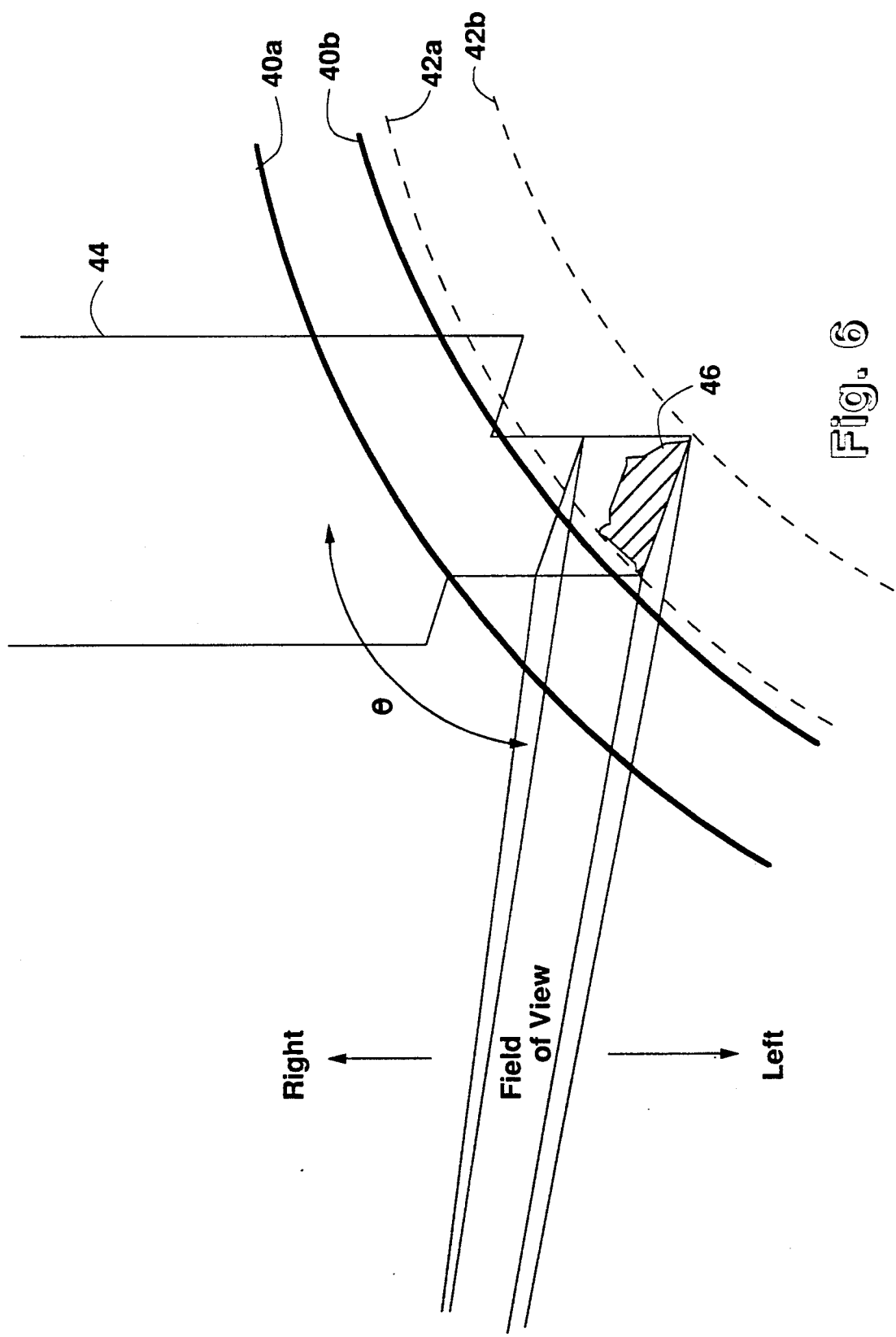
FIG. 6 is a illustration of the laser profile technique used in the inspection system of the present invention to determine the thickness of deposits in grooves of a piston.

One of the novel features of the invention system is the use of laser profilometry to determine the depth of carbon deposits in the piston groove. FIG. 6 is an illustration of the geometry of a laser profilometry system. The piston groove is illustrated by upper groove edges 40a and 40b and by lower groove edges 42a and 42b, shown in phantom. A beam of laser light is illustrated by the generally rectangular profile 44. The camera is aimed at the piston at an angle, with the field of view shown in FIG. 6. The thickness of the deposit 46 in the groove can be calculated using the data processing algorithm described below.

The angle $\theta$ between the incident laser beam and the camera field of view can vary over a fairly wide range so long as the angle is substantially greater than 0°. Excellent results can be obtained with a $\theta$ angle of approximately 45°. From the camera viewpoint, the laser line defines the groove height profile from which carbon thickness can be measured. Given the offset distance of the camera and the camera-laser angle, it is straightforward to calculate the given profile for a given point in the groove. The rotating platform provides the facility to move the piston through 360°, and collect depth information at an arbitrary dense set of points. Although the invention system has been described in connection with the measurement of deposit depths in piston grooves, it can also be adapted to measure deposit thickness on the piston lands.

The laser line may be generated by three different methods: (1) A point source of laser light can be spread in one direction by using a cylindrical lens. (2) A point source of laser light can be directed toward an oscillating mirror. This mirror is typically mounted on a galvanometric movement which is driven by a sinusoidal voltage. In this way, the light is rapidly swept back and forth over the area of interest (the groove). If the camera has the proper aperture speed, the point source will appear as a line of light. The mirror oscillation frequency is typically 600 Hz. (3) A point source of laser light can be directed toward a rotating polygon. The polygon will cause the point source of light to be scanned along a line (similar to (2) above). However, the scan is linearly directed from one line endpoint (A) to the other endpoint (B), rather than sinusoidally directed from A to B to A (back and forth).

Suitable lasers are available in a wide variety of wavelengths. However, in the preferred embodiment, HeNe lasers in the visible and infrared range were used. An optical filter was found to be very useful to subdue ambient room noise. This filter may be a bandpass, centered at the laser frequency, or an optical longpass filter which passes the laser light.

Figure 7:
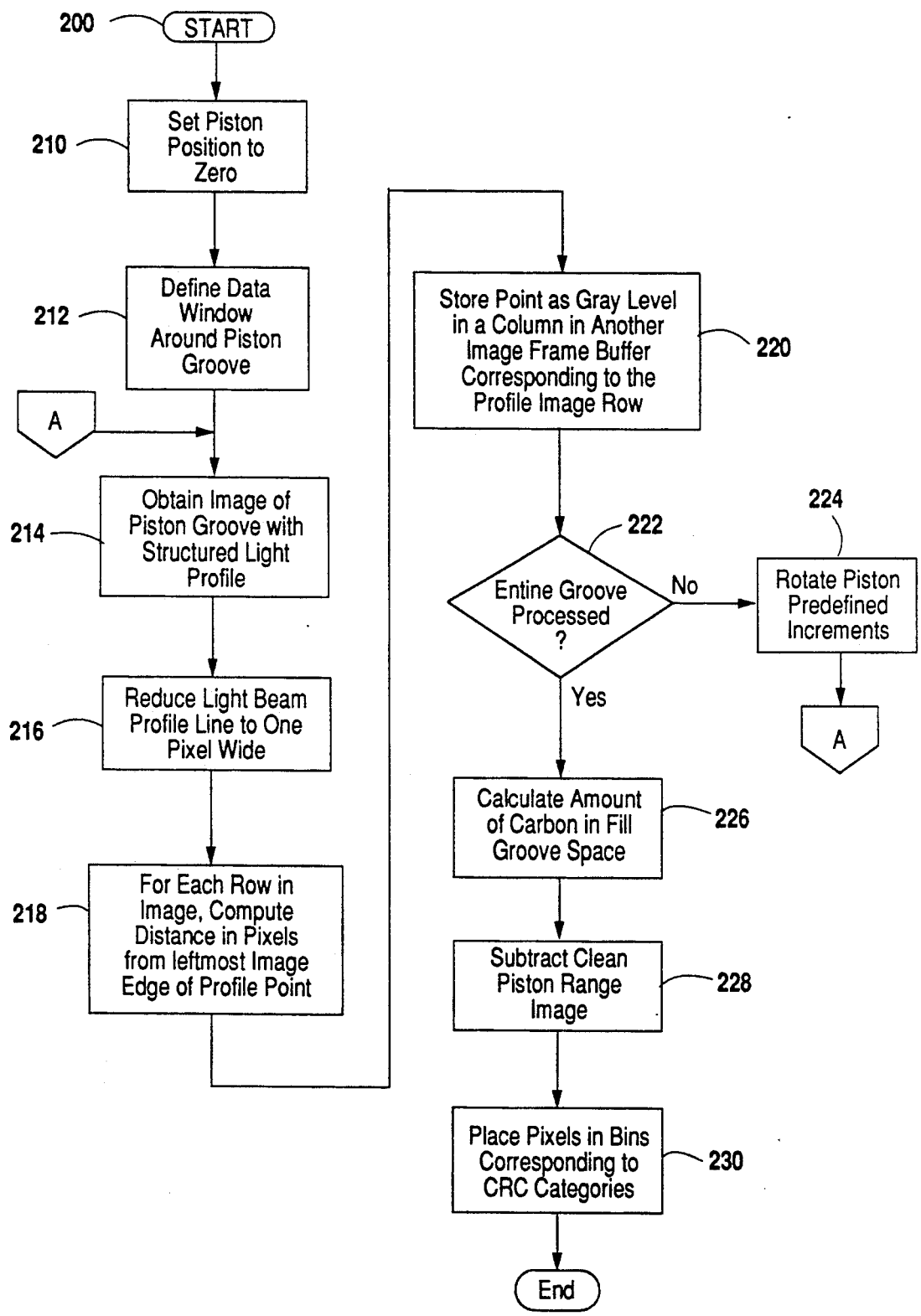
FIG. 7 is a flow chart of the data processing steps implemented in an alternate embodiment of the optical inspection system of the present invention utilizing laser profilometry.

The processing steps implemented by the microprocessor 28 for using laser profilometry to determine the depth of carbon deposits in the piston grooves can be seen by referring to FIG. 7. In step 200, the system is started. In step 210, the initial position of the piston is defined to be zero degrees (0°). In step 212, a data window is defined around the portion of the piston groove to be surveyed. In step 214, the piston groove is illuminated with a structured light profile and an image of the piston groove is obtained. In step 216, the light beam image is reduced to produce a profile line which is one pixel wide. Next, in step 218, for each row in the image, the distance in pixels is computed from the left most image edge to the profile point. This distance will have a digital value between 0 and 255. In step 220, this point is stored as a graylevel in a column in another image frame buffer corresponding to the profile image row. In step 222, a determination is made as to whether the entire groove has been processed. If the entire groove has not been processed, the piston is rotated by a predefined increment in step 224 and steps 214 through 222 are repeated. In the preferred embodiment of the invention, the rotation increment is approximately 2°. If a determination is made that the entire groove has been processed, the amount of carbon in the fill groove space is calculated in step 226. In the preferred embodiment of the invention, 100% of the groove gap space is defined as 90% of the camera horizontal resolution which allows for piston-to-camera placement error. Thus, the percentage fill in the groove is determined as a ratio of the maximum number of pixels possible in the corresponding video image. In step 228, the groove is rated by subtracting a clean piston range image and, in step 30, the pixels are placed in bins corresponding to the CRC categories. CRC rating specifications require that carbon depth must be categorized as clean, light (between 0 and 25% fill), medium (greater than 25% and less than 100% fill), and heavy (100% fill). This categorization can be done with the computed carbon profile data. The profile data may also be used directly for a more accurate carbon volume measurement.

Although the method and apparatus of the present invention has been described in connection with the preferred embodiment, it is not intended to be limited to the specific form set forth herein, but on the contrary, it is intended to cover such modifications, alternatives and equivalents as can reasonably be included within the spirit and scope of the claims.

What is claimed is:

1. An optical system for detecting lacquer and carbon deposits on an internal combustion engine piston, comprising:
    a piston, said piston having a center axis;
    means for rotating said piston;
    means for indirectly illuminating said piston with a quantity of light, said means for illuminating comprising a curved reflector having an opening therein and a plurality of light sources directing light toward said reflector for reflection toward said piston;
    optical sensing means for obtaining an optical image of the surface of said piston and for producing a digital representation thereof, said optical sensing means comprising a lens received through said opening in said curved reflector, said lens having an optical view axis offset from the center axis of said piston;
    means for processing said digital representation of said optical image to obtain a quantitative representation of lacquer or carbon deposits on said piston.

2. The system according to claim 1, said optical sensing means comprising a video camera having a charge coupled device sensor.

3. A method for detecting lacquer and carbon deposits on an internal combustion engine piston, comprising the steps of:
    positioning a piston on a means for rotation, said piston having a circumferential groove therein;
    illuminating said piston with a beam of laser light;
    defining a data window around said groove in said piston;
    obtaining a digital image of the portion of said groove in said data window, said digital image comprising a plurality of pixels;
    processing said digital image to generate a profile line representing the quantity of deposit in said groove;
    rotating said piston until said profile line has been obtained for the entire groove; and
    correlating said profile line with the quantity of material deposited in said groove.

* * * * *